United States Patent
Floriot

(10) Patent No.: US 11,713,268 B2
(45) Date of Patent: Aug. 1, 2023

(54) PERIOD-CODED CONTAINERS WITH A TRACEABLE MATERIAL COMPOSITION

(71) Applicant: Owens-Brockway Glass Container Inc., Perrysburg, OH (US)

(72) Inventor: Philippe Floriot, Vernaison (FR)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 1034 days.

(21) Appl. No.: 16/426,887

(22) Filed: May 30, 2019

(65) Prior Publication Data

US 2020/0378935 A1    Dec. 3, 2020

(51) Int. Cl.
*G01N 23/22* (2018.01)
*C03B 9/14* (2006.01)
*C03C 3/087* (2006.01)
*C03C 3/095* (2006.01)
*G01N 23/223* (2006.01)
*G01N 33/38* (2006.01)
*C03C 4/12* (2006.01)
(Continued)

(52) U.S. Cl.
CPC ............ *C03B 9/14* (2013.01); *C03B 1/00* (2013.01); *C03C 3/087* (2013.01); *C03C 3/095* (2013.01); *C03C 4/00* (2013.01); *C03C 4/12* (2013.01); *G01N 23/223* (2013.01); *G01N 33/386* (2013.01); *G01N 2223/0766* (2013.01); *G01N 2223/301* (2013.01); *G01N 2223/302* (2013.01); *G01N 2223/304* (2013.01); *G01N 2223/615* (2013.01); *G01N 2223/616* (2013.01)

(58) Field of Classification Search
CPC ............... G01N 23/223; G01N 33/386; G01N 2223/0766; C03C 3/095
USPC ........................................................ 65/29.12
See application file for complete search history.

(56) References Cited

U.S. PATENT DOCUMENTS

| 4,125,405 A | 11/1978 | Araujo et al. |
| 4,337,183 A | 6/1982 | Santiago |
| 6,313,053 B1 | 11/2001 | Shelestak |

(Continued)

FOREIGN PATENT DOCUMENTS

| EP | 1270091 A1 | 1/2003 |
| EP | 1491350 A2 | 12/2004 |

OTHER PUBLICATIONS

Christopher Latkoczy, et al., Title: Development and Evaluation of a Standard Method for the Quantitative Determination of Elements in Float Glass Samples by LA-ICP-MS, Journal of Forensic Sciences, vol. 50, No. 6, Nov. 2005 (Nov. 2005), pp. 1-15, XP055725630.

(Continued)

*Primary Examiner* — Christopher M Raabe

(57) ABSTRACT

A system and method for producing period-coded glass containers is disclosed. One method comprises producing a glass container from a traceable material composition associated with a predetermined time period, manufacturing facility, and/or time of container manufacture, where the glass container is configured to be analyzed for the traceable material composition, and at least one of constituents of or amounts of materials in the traceable material composition is configured to be identified and cross-referenced to a cross-reference schedule for identifying the time period, manufacturing facility, and/or time of container manufacture in which the glass container was produced.

22 Claims, 2 Drawing Sheets

(51) Int. Cl.
*C03B 1/00* (2006.01)
*C03C 4/00* (2006.01)

(56) References Cited

U.S. PATENT DOCUMENTS

| | | |
|---|---|---|
| 7,256,398 B2 | 8/2007 | Ross et al. |
| 9,746,424 B2 | 8/2017 | Leconte et al. |
| 9,982,884 B2 | 5/2018 | Huber et al. |
| 11,043,058 B2 | 6/2021 | Temboury et al. |
| 2006/0131517 A1* | 6/2006 | Ross ............... G06V 20/66 |
| | | 250/556 |
| 2006/0131518 A1 | 6/2006 | Ross et al. |
| 2007/0259767 A1 | 11/2007 | Siebers et al. |
| 2009/0302101 A1 | 12/2009 | Poizat et al. |
| 2013/0341228 A1 | 12/2013 | Click et al. |
| 2014/0116911 A1 | 5/2014 | Bryant |
| 2017/0061350 A1* | 3/2017 | Smith ............ G06F 16/9554 |
| 2017/0166474 A1 | 6/2017 | Debbage et al. |
| 2017/0341812 A1 | 11/2017 | DeMartino et al. |
| 2018/0105446 A1 | 4/2018 | Faulkinbury et al. |
| 2019/0219526 A1* | 7/2019 | Mazurkiewicz ..... G01N 23/223 |

OTHER PUBLICATIONS

Int. Search Report and Written Opinion, Int. Application No. PCT/US2020/034031, Int. Filing Date: May 21, 2020, Applicant: Owens-Brockway Glass Container Inc., dated Sep. 11, 2020.

Colombian Office Action, Serial No. NC2021/0016186, Applicant: Owens-Brockway Glass Container Inc., dated Mar. 27, 2023.

\* cited by examiner

US 11,713,268 B2

PERIOD-CODED CONTAINERS WITH A TRACEABLE MATERIAL COMPOSITION

TECHNICAL FIELD

The present disclosure is directed to containers and, more particularly, to methods for identifying a period of production of a container.

BACKGROUND

Glass containers are typically composed of a 90% or greater soda-lime-silica base composition including silicon oxide, calcium oxide, and sodium oxide. The composition also can include aluminum oxide, magnesium oxide, titanium oxide, iron oxide, barium oxide, potassium oxide, chromium oxide, and manganese oxide. The glass containers can be filled with a product and then transported to another location. Additionally, the containers can be authenticated and tracked to ensure proper delivery.

BRIEF SUMMARY OF THE DISCLOSURE

The present disclosure embodies a number of aspects that can be implemented separately from or in combination with each other.

In accordance with one aspect of the disclosure, a method of producing period-coded glass containers is provided that includes selecting a first traceable material composition; producing glass containers from the first traceable material composition for a first period; selecting a second traceable material composition different from the first traceable material composition; producing glass containers from the second traceable material composition for a second period; producing a cross-reference schedule of traceable material compositions, time periods, manufacturing facilities, or times of container manufacture in which the traceable material compositions are used in production of glass containers; analyzing a glass container for material composition; identifying at least one of constituents of or amounts of materials in the material composition of the analyzed glass container; and cross-referencing the identified at least one of constituents or amounts of materials in the material composition to the cross-reference schedule to identify at least one of a time period, a manufacturing facility, or a time in which the analyzed glass container was produced. The traceable material can also be used to identify the glass manufacturing facility that manufactured the container, as well as the period in which the container was made at such facility. As used herein, the term "period-coded" refers to a specific time period as well for the glass manufacturing facility at which the container was made.

In accordance with another aspect of the disclosure, a method of identifying a glass container production time period is provided that includes analyzing a glass container for a traceable material composition, where the traceable material composition is associated with at least one of a predetermined time period, a manufacturing facility, or a time of glass container manufacture; identifying at least one of constituents of or amounts of materials in the traceable material composition of the analyzed glass container; and cross-referencing the identified at least one of constituents or amounts of materials in the traceable material composition to a cross-reference schedule to identify at least one of the time period, the manufacturing facility, or the time in which the analyzed glass container was produced.

In accordance with another aspect of the disclosure, a method for producing period-coded glass containers is provided that includes producing a glass container from a traceable material composition associated with at least one of a predetermined time period, a manufacturing facility, or a time of manufacture, where the glass container is configured to be analyzed for the traceable material composition, and at least one of constituents of or amounts of materials in the traceable material composition is configured to be identified and cross-referenced to a cross-reference schedule for identifying at least one of the time period, the manufacturing facility, or the time in which the glass container was produced.

BRIEF DESCRIPTION OF THE DRAWINGS

The disclosure, together with additional objects, features, advantages and aspects thereof, will be best understood from the following description, the appended claims, and the accompanying drawings, in which:

DETAILED DESCRIPTION

A general object of the present disclosure, in accordance with at least one aspect of the disclosure, is to provide methods for producing and/or identifying period-coded glass containers.

Traceability and authentication of glass containers can include marking the containers with a code or other identifying feature as they are manufactured. Using a code or other identifying feature on each container can be used to determine, for example, a product in the container, filling date, or other characteristics. Additionally, containers with identifying features or codes can be used for anti-counterfeiting efforts. Employing the methods and containers described herein improves the ability to identify and track a time period, a manufacturing facility, and/or a time of container production and prevent container counterfeiting.

Figure 1:
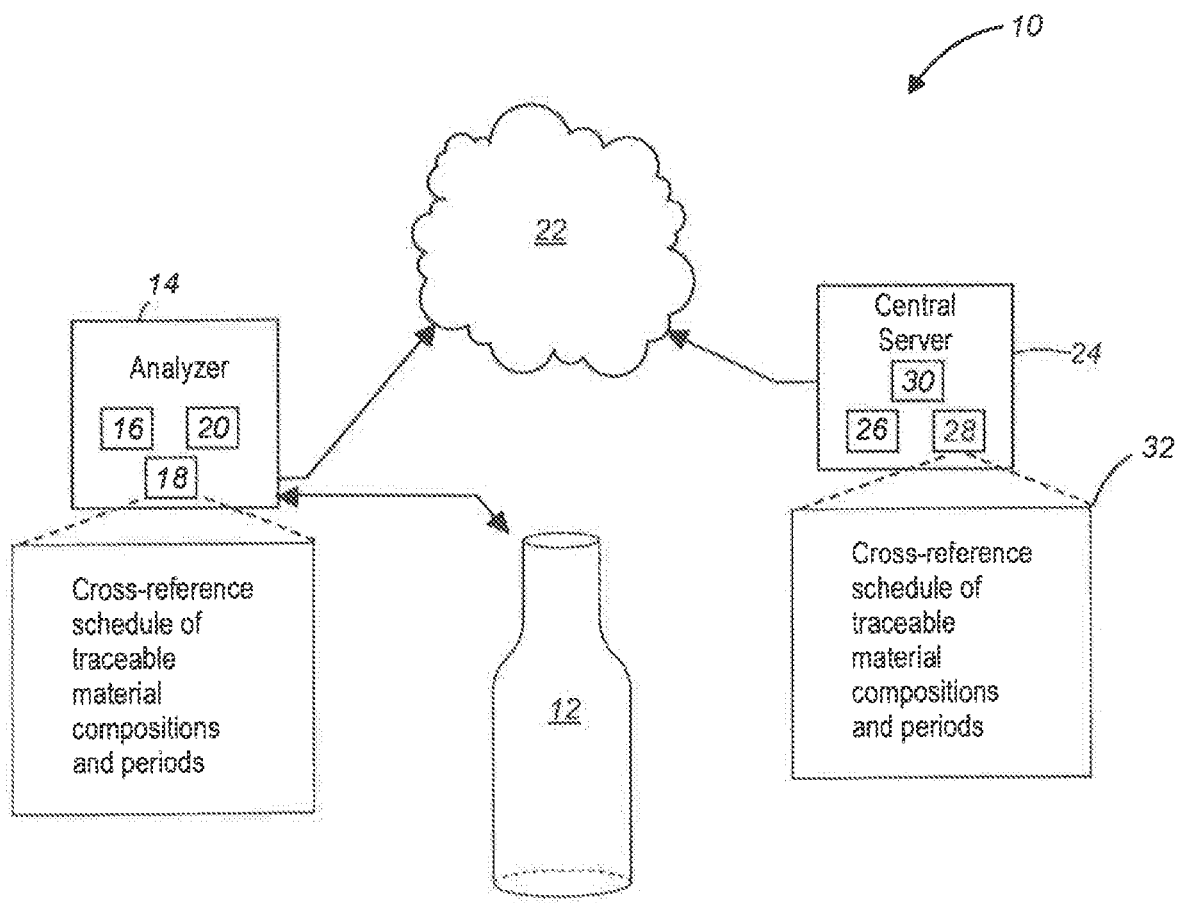
FIG. 1 is a diagrammatic view illustrating a system for producing a period-coded container from a traceable material composition, in accordance with an illustrative embodiment of the present disclosure.

FIG. 1 depicts an operating environment comprising a system 10 for implementing the method disclosed herein. The system 10 may include a central server 24, an analyzer 14 electrically connected to (e.g., wireless or over a wired network) and configured for communication with the central server 24, and a database 32 that is part of and/or accessible by the central server 24. It will be appreciated that the disclosed method can be used with any number of different systems and is not specifically limited to the operating environment shown in FIG. 1. The following paragraphs provide a brief overview of one illustrative embodiment of the system 10; however, other systems not shown here could employ or perform the disclosed method as well.

The system 10 and operating environment shown in FIG. 1 can be used for producing a period-coded glass container 12 using a traceable material composition. The glass container 12 may include, for example, a bottle, a jar, a jug, a food or beverage container, or another suitable container in which a variety of goods or products may be packaged, including, for example and without limitation, various types of food products and other liquids, gels, powders, particles, and the like. For example, the glass container 12 can be formed of glass for packaging goods/products. The glass container 12 may be fabricated using a number of manufacturing processes depending on the material from which the container is formed. For example, when formed of glass, the glass container 12 may be fabricated using a press-and-blow, blow-and-blow, or hand blowing manufacturing process. It will be appreciated that the present disclosure is not intended to be limited to containers of any particular material(s) or any particular manufacturing process. In a specific embodiment, the glass container 12 comprises a container formed of glass.

Typical glass containers can be composed of a 90% or greater soda-lime-silica base composition including silicon oxide, calcium oxide, and sodium oxide. The glass container composition also typically includes aluminum oxide, magnesium oxide, titanium oxide, iron oxide, barium oxide, potassium oxide, chromium oxide, and/or manganese oxide. One example of a conventional soda lime glass container composition can include about 74% silicon dioxide, 13% sodium oxide, 10.5% calcium oxide, 1.3% aluminum oxide, 0.3% potassium oxide, 0.2% magnesium oxide, 0.04% ferric oxide, 0.01% titanium dioxide, and 0.2% sulfur trioxide. It is contemplated that a conventional glass container composition may include a variety of other compositions or amounts of components.

The glass container 12 can include a traceable material composition associated with a predetermined time period, manufacturing facility, and/or a time of container manufacture. The traceable material composition can be detected by the analyzer 14. The traceable material composition can include one or more tracer elements or materials in a small quantity (e.g., three times the concentration usually found in glass, less than 0.5% of the overall glass container composition). The tracer elements may include raw materials often used in typical glass container production, for example selenium, cobalt, manganese, vanadium, barium, copper, and the like. Additionally, the tracer elements may include rare earth elements, for example scandium, yttrium, lanthanum, cerium, praseodymium, neodymium, promethium, samarium, europium, gadolinium, terbium, dysprosium, holmium, erbium, thulium, ytterbium, and/or lutetium. In some instances, the tracer elements can be introduced as metal, or oxide, or in combination with other elements (for example as a carbonate or sulfate). Other exemplary materials that may be used in the traceable material composition can include zinc, strontium, titanium, barium, and bismuth whatever the form of introduction (oxide, carbonate, sulfate, and the like). For example, TiO2 is typically present at approximately 0.05% in glass containers. The traceable material composition can be designed to be non-toxic and not alter the intrinsic properties of the glass and/or its neutrality.

The traceable material composition concentration in the glass container 12 can be significantly higher than the usual level in container glass and can be distinguishable from other elements that are naturally present or present as impurities in container glass but still sufficiently low so that a third party (e.g., a counterfeiter) may not suspect the presence of the traceable material composition. The traceable material composition can include one or more materials not used in conventional container glass compositions, or one or more conventional container glass constituents in amounts or ratios not used in conventional container glass compositions. The traceable material composition can be configured to not modify the color or appearance of the glass container 12 and may not be visually detected. Additionally, the traceable material composition can be configured to not alter the intrinsic properties or the neutrality of the glass container 12.

As illustrated in FIG. 1, the system 10 can include an appropriately configured hand-held analyzer 14 to detect and identify constituents of and/or amounts of materials in the traceable material composition. In an example, the analyzer 14 may include a portable x-ray analyzer (e.g., X-ray fluoroscope) capable of detecting the tracer elements in the glass container 12 in small concentrations (e.g., several parts per million). The portable x-ray analyzer can use x-ray fluorescence (XRF), which includes a process whereby electrons are displaced from their atomic orbital positions thereby releasing energy that is characteristic of a specific element. The released energy can be detected by the x-ray analyzer, which can in turn categorize the released energy by element. For example, the hand-held analyzer 14 can be used to expose the glass container 12 to x-ray fluorescence and can detect energy released by at least one tracer element in the glass container 12. The respective elements in the glass container 12 can then be determined and/or categorized based on the detected energy. A cross-reference schedule of traceable material compositions and corresponding time periods, manufacturing facilities, and/or times of manufacture can then be used to determine a specific time period, manufacturing facility, and/or time of manufacture of the glass container 12. The analyzer 14 may be configured to transmit information to and/or from a central server 24 over a network 22 (e.g., to and/or from a database 32 in network 22). The analyzer 14 is not restricted to an x-ray analyzer, but may comprise or include any number of devices known in the art configured for detecting and/or analyzing the traceable material composition. It will be appreciated that the system 10 and the associated environment may include a single analyzer or a plurality of analyzers, which can be located and/or used at different points throughout the distribution chain.

The cross-reference schedule of traceable material compositions can be produced and/or configured when each glass container 12 is manufactured. Each traceable material composition can be associated with a specific time period (e.g., a year, a month, and the like), a manufacturing facility, a container shape, a container mold number, a time of manufacture, and/or other associated manufacturing data records. For example, a glass container 12 with a first traceable material composition can be fabricated during a first year, and a glass container 12 with a second traceable material composition can be fabricated during a second year. When the analyzer 14 analyzes the glass container 12 having the first traceable material composition, it can be determined that the glass container 12 was fabricated in the first year. When the analyzer 14 analyzes the glass container 12 with the second traceable material composition, it can be determined that the glass container 12 was fabricated in the second year. It will be appreciated that each respective traceable material composition may be associated with different time periods, manufacturing facilities, times of manufacture, and/or other associated manufacturing data. The cross-reference schedule can be stored by the analyzer 14 and/or stored in a database 32 residing on a central server 24, where the cross-reference schedule can be used for identifying the time period, the manufacturing facility, and/or the manufacturing time in which a glass container 12 was manufactured and/or other associated manufacturing data at least partially based on the detected traceable material composition in the glass container 12.

As illustrated in FIG. 1, the analyzer 14 may comprise any suitable apparatus that may include an electronic processor or processing device 16, an electronic memory device 18 that is part of and/or accessible by the processing device 16, a communications interface 20, and/or other suitable hardware and software.

The analyzer 14 may include an application configured to be coded for analyzing a traceable material composition and determining a time period, a manufacturing facility, and/or a time of manufacture associated with the glass container 12. With regard to the application, the application can be configured to perform the method steps herein. For example, the analyzer 14 may include means for detecting and analyzing the traceable material composition in the glass container 12. In an embodiment, the analyzer 14 can include a hand-held x-ray analyzer that may have internet connectivity. In any event, the analyzer 14 may comprise any traceable material composition device and may include a combination of hardware, software, and/or other components that enables the detecting and determining a traceable material composition, among potentially other functionality.

The analyzer 14 may further be configured to transmit information about the traceable material composition to the central server 24 over the network 22 and to receive and/or analyze received information from the central server 24 over network 22. For example, the analyzer 14 can obtain information about detected tracer element energy using x-ray fluorescence and may transmit that information to the central server 24 over network 22 for information processing and/or storage.

The processing device 16 of the analyzer 14 may include any type of suitable electronic processing device (e.g., programmable microprocessor, microcontroller, central processing unit (CPU), application specific integrated circuit (ASIC), etc.) that is configured to process data and/or execute appropriate programming instructions for software, firmware, programs, applications, algorithms, scripts, etc., necessary to perform various functions of the analyzer 14. The memory device 18 may include, for example, random access memory (RAM), read only memory (ROM), hard disk(s), universe serial bus (USB) drive(s), memory card(s), or any type of suitable electronic memory means (e.g., non-transitory computer-readable medium with instructions stored thereon) and may store a variety of data. This includes, for example, software (e.g., code or logic), firmware, programs, applications, algorithms, scripts, etc., required to perform functions of the analyzer 14.

In at least certain embodiments, the analyzer 14 may also include one or more components to enable a user to manually provide or input certain data. This data may include, for example, container manufacture date, traceable material composition associated with the glass container 12, and other useful data. More particularly, the analyzer 14 may include a user interface (not shown), for example and without limitation, a touch screen, keypad, keyboard, etc., that a user may utilize and/or manipulate to provide data or information relating to one or more glass containers. The analyzer 14 may further include a communications interface 20 that may include or be electrically connected to certain communication-supporting infrastructure (e.g., one or more known components/devices, for example, routers, modems, antennas, electromechanical ports, transceivers, etc.) to allow for the communication and exchange of data between the analyzer 14 and one or more other components of the system 10, for example, the central server 24. The central server 24 may be configured to receive or transmit information from or to the analyzer 14, respectively.

In some instances, the central server 24 may be used to control, govern, and/or manage certain operations or functions of the system 10, including performing or facilitating some or all of the functionality of the method described herein. The central server 24 may be a standalone component or part of either another component or a larger system or network. Further, the central server 24 may comprise a single server element or a plurality of server elements. In the latter instance, the individual server elements may be electrically connected to each other to allow communication therebetween. The central server 24 may be implemented with a combination of hardware, software, firmware, and/or middleware, and, in an illustrated embodiment, may include one or more electronic processors or processing devices 26 and one or more electronic memory devices 28. In an embodiment, the memory device 28 may be a component of the processing device 26, while in another embodiment, it may be separate and distinct therefrom but accessible thereby.

Similar to the processing device 16 of the analyzer 14, the processing device 26 may comprise any type of suitable electronic processor or processing device (e.g., programmable microprocessor, microcontroller, center processing unit (CPU), application specific integrated circuit (ASIC), etc.) that is configured to receive and process data and/or execute appropriate programming instructions for software, firmware, programs, algorithms, scripts, etc., to perform various functions, for example and without limitation, those relating to the method described herein. The central server 24 and/or the processing device 26 may further include an input/output (I/O) or at least one communication interface 30 through which input and output signals may pass, for example, those communicated between the analyzer 14 and the central server 24 or between the central server 24 and other components that may or may not be part of the system 10. The communication interface 30 may include, or be electrically connected to and configured for communication with, certain communication-supporting infrastructure (e.g., one or more known components/devices, for example, routers, modems, antennas, electrical ports, transceivers, etc.), and is/are configured to communicate with various components of the system 10 via a public or private network or using other suitable communication techniques or protocols including, but not limited to, one or more of those described herein.

The memory device 28 may include, for example, random access memory (RAM), read only memory (ROM), hard disk(s), universe serial bus (USB) drive(s), memory card(s), or any type of suitable electronic memory means (e.g., non-transitory computer-readable medium with instructions stored thereon) and may store a variety of data. This includes, for example, software (e.g., code or logic), firmware, programs, algorithms, scripts, and other electronic instructions that, for example, are required to perform one or more of the functions described herein; and, in an embodiment, various data structures (e.g., databases, for example, database 32) for storing various information and data, including that required to perform some or all of the functions or method described herein.

As will be described in greater detail below, the central server 24 may be configured and operable to receive data from one or more other components of the system 10 (e.g., analyzer 14), and to store the received data in one or more database 32 stored in a suitable electronic memory device, for example and without limitation, the memory device 28 of the central server 24. Additionally, in at least certain embodiments, the central server 24 may also be configured to process and compile data that it receives and/or that is stored in the database 32, to generate reports relating to the received/stored data, to generate and/or interface with user interfaces displayed on a display device associated with the central server 24 and/or the analyzer 14 to provide data to and/or receive data from a user of the system 10.

While certain analyzers and arrangements relating thereto have been described herein, it will be appreciated that the present disclosure is not limited to the use of any particular type of analyzer(s) or corresponding arrangement(s). Additionally, the system 10 may include and/or be configured to support any number of analyzers. As will be appreciated in view of the description of the method set forth below, the analyzer 14 may be distributed at different points or locations throughout a distribution chain in which glass containers travel (e.g., customer, consumer/end user, return/collection center, etc.). Accordingly, the system 10 may include one or a plurality of analyzers, and thus, is not limited to any particular number of analyzers 14.

As briefly described above, various components of the system 10 may be configured to communicate with each other to exchange data therebetween. This communication may be facilitated across a suitable communications network through communication interfaces of the individual components. The communications network 22 may comprise a wired and/or wireless network, for example, one or a combination of: a suitable Ethernet network; radio and telecommunications/telephone networks (e.g., cellular networks, analog voice networks, or digital fiber communications networks); or any other suitable type of network and/or protocol (e.g., local area networks (LANs), wireless LANs (WLANs), broadband wireless access (BWA) networks, personal area networks (PANs), publicly switched telephone networks (PSTNs), etc.). The communications network 22 may be configured for use with one or more standard communications technologies and protocols, and may utilize links using known technologies, for example, Ethernet, integrated services digital network (ISDN), digital subscriber line (DSL), as well as other known communications technologies. Similarly, the networking protocols used on a network to which some or all of the components of the system 10 are interconnected may include multi-protocol label switching (MPL), the user datagram protocol (UDP), the hypertext transport protocol (HTTP), the simple mail transfer protocol (SMTP), and the file transfer protocol (FTP), among other suitable network protocols. In an embodiment, the transmission control protocol/Internet protocol (TCP/IP) may be used, in which case it will be appreciated that each component configured for communication using such a protocol can be configured with a static IP address or can be set up to automatically receive an assigned IP address from another device on the network. Further the data exchanged over such the network 22 may be represented using technologies, languages, and/or formats, for example, the hypertext markup language HTML), the extensile markup language (XML), and the simple object access protocol (SOAP) among other suitable data representation technologies. Accordingly, it will be appreciated in view of the foregoing that the communication between various components of the system 10 may be facilitated in any number of ways using any number of techniques, and therefore, the present disclosure is not limited to any particular way or technique(s); rather any suitable way or technique may be utilized.

The database 32 may be located and/or stored in or on a suitable electronic memory device, for example, the memory device 28 of the central server 24 or another suitable memory device of and/or accessible by the central server 24. The present disclosure is not intended to be limited to the database 32 being stored in or on any particular memory device.

Figure 2:
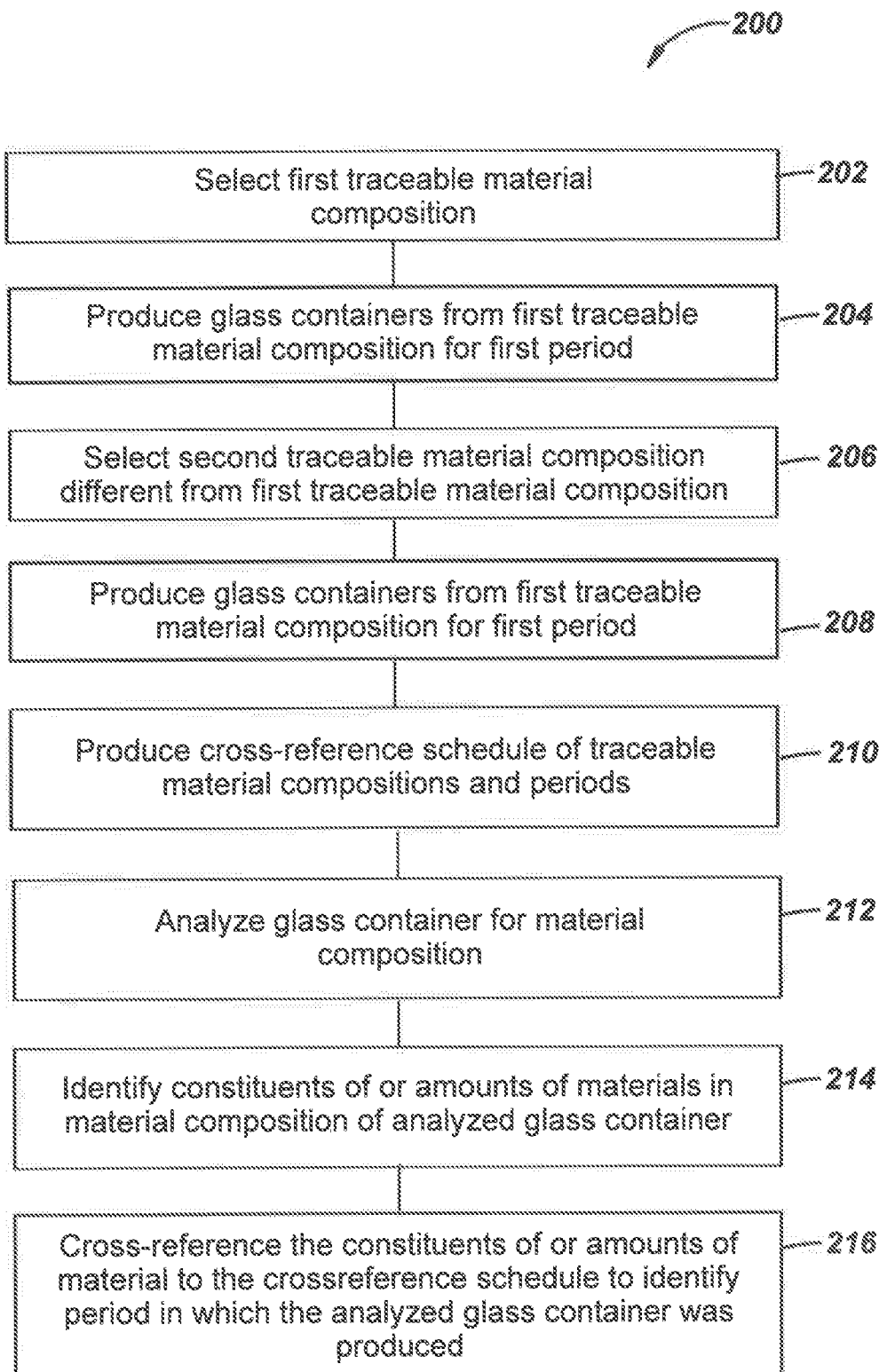
FIG. 2 is a flow diagram showing various steps of an illustrative embodiment of a method using the system for producing the period-coded container from a traceable material composition in FIG. 1.

FIG. 2 illustrates an example of a method 200 of producing period-coded glass containers. For purposes of illustration and clarity, method 200 will be described in the context of the glass container 12 and the operating environment of the system 10 described above and illustrated in FIG. 1. It will be appreciated, however, that the application of the present methodology is not meant to be limited solely to such a glass container and/or operating environment, but rather method 200 may find application with any number of containers and operating environments. It will be further appreciated that while steps of the methodology may be described in a particular order or and/or as being performed by particular components, unless otherwise noted, the present disclosure is not limited to any particular order and/or number of steps or to any particular components performing the steps.

In an embodiment, method 200 comprises a step 202 of selecting a first traceable material composition. Selecting the first traceable material composition can include selecting at least one tracer element to be used in the production of the glass container 12. In an example, lanthanum can be selected as the tracer element at a concentration that is three times or greater than the amount normally found in glass containers. In another example, a combination of lanthanum and vanadium can be selected as the tracer elements. It will be appreciated that selecting the first traceable material composition can include selecting any tracer element or combination of tracer elements at any concentration greater than naturally occurring in glass. Selecting the first traceable material composition may be performed by the processor 16 of the analyzer 14 and/or the processor 26 of the central server 24.

Once the first traceable material composition is selected, method 200 includes a step 204 of producing glass containers from the selected first traceable material composition for a first period for a given manufacturing facility. Producing glass containers can include various processes, for example press-and-blow, blow-and-blow, and/or using individual section (IS) equipment. The first period can include a predetermined time period (e.g., a year, a month, a number of days, and the like). In an example, a glass melter can be used to melt glass raw materials including the first traceable material composition, and an individual section machine can be used to form the molten glass into a glass container 12, where the first traceable material composition has been predetermined to represent a first year and a given manufacturing facility. It will be appreciated that the glass containers can be manufactured using other equipment and other processes.

Method 200 further comprises a step 206 of selecting a second traceable material composition that is different from the first traceable material composition. Selecting the second traceable material composition can include selecting at least one tracer element to be used in the production of a glass container 12. Continuing with the above example, cobalt oxide can be selected as the second traceable material composition at a concentration that is three times greater than the amount normally found in glass containers. It will be appreciated that selecting the second traceable material composition can include selecting any tracer element or combination of tracer elements different from the first traceable material composition. Selecting the second traceable material composition may be performed by the processor 16 of the analyzer 14 and/or the processor 26 of the central server 24.

Method 200 further comprises a step 208 of producing glass containers from a second traceable material composition for a second period for a given manufacturing facility. Similar to producing glass containers from a first traceable material composition, producing glass containers from a second traceable material composition can include using various processes, for example press-and-blow, blow-and-blow, and/or individual section (IS) equipment. The second period can include a predetermined time period (e.g., a year, a month, a number of days, and the like). In an example, a glass melter can be used to melt glass raw materials including the second traceable material composition, and an individual section machine can be used to form the molten glass into a glass container 12, where the second traceable material composition has been predetermined to represent a second year and a given manufacturing facility. It will be appreciated that the glass containers can be manufactured using other equipment and other processes.

Method 200 further comprises a step 210 of producing a cross-reference schedule of traceable material compositions and periods. Producing the cross-reference schedule of traceable material compositions and periods can include using, for example, the analyzer 14 to collect and gather data regarding the traceable material compositions and associated time periods, manufacturing facilities, and/or times of container manufacture. As the glass containers 12 are manufactured, the analyzer 14 and/or central server 24 can receive information that may include the traceable material composition and/or the corresponding time period, manufacturing facility, and/or time of container manufacture. Continuing with the example above, the cross-reference schedule can be produced by compiling the first traceable material composition of lanthanum and the associated first time period of the first year and manufacturing facility and the second traceable material composition of cobalt oxide and the associated second time period of the second year and manufacturing facility. It will be appreciated that producing the cross-reference schedule may include additional traceable material compositions associated with additional time periods, manufacturing facilities, and/or times of container manufacture. Producing the cross-reference schedule of traceable material compositions may be performed by the processor 16 of the analyzer 14 and/or the processor 26 of the central server 24.

Method 200 further comprises a step 212 of analyzing a glass container for material composition. Analyzing the glass container can include using a non-destructive, hand held x-ray analyzer 14 to expose the glass container 12 to x-ray fluorescence and detect energy released from displaced electrons from the glass components and the traceable material composition. As the analyzer 14 receives/detects the released energy, the analyzer 14 can record and/or store information including the amounts of released energy detected. Additionally, analyzing the glass container for material composition may include using other techniques or equipment, for example, inductively coupled plasma (ICP) and/or energy-dispersive x-ray spectroscopy (EDX). In these instances, the glass container may be initially analyzed using a hand held x-ray analyzer 14 to determine the material composition. A second glass container from the same batch can be analyzed for material composition using a more accurate device and method, for example those described above, which may be destructive to the second glass container. The results from the more accurate method and the second glass container can be transmitted to and recorded in the cross-reference schedule and/or the database 32 for further cross-referencing with results from the initial analysis. In some instances, the central server 24 may store the information.

Method 200 further comprises a step 214 of identifying at least one constituent of or amounts of materials in the traceable material composition of the analyzed glass container 12. Each material releases a certain amount of energy when exposed to x-ray fluorescence. Identifying the constituents and/or amounts of materials in the traceable material composition can include correlating the detected amounts of released energy of a tracer element with empirical data to determine and identify each tracer element and/or amounts of elements based on the amount of released energy. For example, the analyzer 14 can detect and/or record an amount of released energy from a glass container 12 using x-ray fluorescence. The analyzer 14 can then correlate the amount of released energy with a specific concentration of the element lanthanum, for example, which indicates that the analyzed glass container 12 includes that specific concentration of lanthanum. It will be appreciated that a variety of constituents and/or amounts of materials can be identified. Identifying the constituent(s) and/or the amounts of materials may be performed by the processor 16 of the analyzer 14 and/or the processor 26 of the central server 24.

Method 200 may further comprise a step 216 of cross-referencing the constituents of and/or amounts of material in the glass container 12 to the cross-reference schedule to identify a period and manufacturing facility in which the analyzed glass container 12 was produced. The identified constituents and/or amounts of materials can be cross-referenced to the cross-reference schedule by comparing the identified constituents and/or amounts of materials with traceable material compositions in the cross-reference schedule. When the identified constituents and/or amounts of materials match with a specific traceable material composition, the analyzed glass container 12 can be determined to have been manufactured in the time period at a given facility associated with that specific traceable material composition. In one example, the analyzer 14 can identify a specific concentration of cobalt oxide in the glass container 12. The specific concentration of cobalt oxide can then be cross-referenced with the cross-reference schedule and matched with the second traceable material composition of cobalt oxide. The time period and facility of manufacture of the glass container 12 can then be identified as the second year from a given manufacturing facility from the cross-reference schedule because the second year and specific facility was predetermined as the time period and facility in which the glass container 12 with the second traceable material composition was manufactured. Cross-referencing the constituents of or amounts of material to the cross-reference schedule can be performed by the processor 16 of the analyzer 14 and/or the processor 26 of the central server 24.

A benefit of using the above method 200 for producing period-coded glass containers is the ability to non-destructively analyze each glass container 12 and identify a time period, given manufacturing facility, and/or time of production using a traceable material composition, which can contribute to anti-counterfeiting efforts. The traceable material composition may not be naturally or significantly present in the standard chemical composition of the glass container 12 and may be known only by the manufacturer and a customer while being unsuspected by a third party.

There thus has been disclosed a system and methods for producing period-coded glass containers that fully satisfy one or more of the objects and aims previously set forth. The disclosure has been presented in conjunction with several illustrative embodiments, and additional modifications and variations have been discussed. Other modifications and variations readily will suggest themselves to persons of ordinary skill in the art in view of the foregoing discussion. For example, the subject matter of each of the embodiments is hereby incorporated by reference into each of the other embodiments, for expedience. The disclosure is intended to embrace all such modifications and variations as fall within the spirit and broad scope of the appended claims.

The invention claimed is:

1. A method of producing period-coded glass containers, comprising:
    selecting a first traceable material composition;
    producing glass containers from the first traceable material composition for a first period;
    selecting a second traceable material composition different from the first traceable material composition;
    producing glass containers from the second traceable material composition for a second period;
    producing a cross-reference schedule of traceable material compositions, time periods, manufacturing facilities, or times of container manufacture in which the traceable material compositions are used in production of glass containers;
    analyzing a glass container for material composition;
    identifying at least one of constituents of or amounts of materials in the material composition of the analyzed glass container; and
    cross-referencing the identified at least one of constituents of or amounts of materials in the material composition to the cross-reference schedule to identify at least one of a time period, a manufacturing facility, or a time in which the analyzed glass container was produced.

2. The method set forth in claim 1, wherein the traceable material compositions include one or more materials not used in conventional container glass compositions, or one or more conventional container glass constituents in amounts or ratios not used in conventional container glass compositions.

3. The method set forth in claim 2, wherein the one or more materials is at least three times the amount used in conventional container glass compositions.

4. The method set forth in claim 1, wherein each constituent in the traceable material compositions comprises less than 0.5% of the glass container.

5. The method set forth in claim 1, wherein the traceable materials include at least one of selenium, cobalt, manganese, copper, vanadium, zinc, titanium, strontium, barium, molybdenum and bismuth.

6. The method set forth in claim 1, wherein the traceable material composition includes an oxide.

7. The method set forth in claim 1, wherein the traceable material composition includes a rare earth element.

8. The method set forth in claim 7, wherein the traceable material composition includes at least one of scandium, yttrium, lanthanum, cerium, praseodymium, neodymium, promethium, samarium, europium, gadolinium, terbium, dysprosium, holmium, erbium, thulium, or ytterbium.

9. The method set forth in claim 1, wherein the analyzing step is carried out using an X-ray analyzer.

10. The method set forth in claim 1, wherein the time period is one year.

11. A method of identifying a glass container production time period, comprising:
    analyzing a glass container for a traceable material composition, where the traceable material composition is associated with at least one of a predetermined time period, a manufacturing facility, or a time of glass container manufacture;
    identifying at least one of constituents of or amounts of materials in the traceable material composition of the analyzed glass container; and
    cross-referencing the identified at least one of constituents of or amounts of materials in the traceable material composition to a cross-reference schedule to identify at least one of the time period, the manufacturing facility, or the time in which the analyzed glass container was produced.

12. The method set forth in claim 11, wherein the time period is one year.

13. The method set forth in claim 11, wherein the analyzing step is carried out using an X-ray analyzer.

14. The method set forth in claim 11, wherein the traceable material composition includes a rare earth element.

15. The method set forth in claim 11, wherein each constituent in the traceable material compositions comprises less than 0.5% of the glass container.

16. A method of producing period-coded glass containers, comprising:
    producing a glass container from a traceable material composition associated with at least one of a predetermined time period, a manufacturing facility, or a time of manufacture,
    where the glass container is configured to be analyzed for the traceable material composition, and at least one of constituents of or amounts of materials in the traceable material composition is configured to be identified and cross-referenced to a cross-reference schedule for identifying at least one of the time period, the manufacturing facility, or the time in which the glass container was produced.

17. The method set forth in claim 16, wherein the traceable material composition includes a rare earth element.

18. The method set forth in claim 16, wherein the time period is one year.

19. The method set forth in claim 16, wherein each constituent in the traceable material composition comprises less than 0.5% of the glass container.

20. The method set forth in claim 1, wherein the first and the second traceable material compositions do not modify the color or the appearance of the glass containers and are not visually detectable.

21. The method set forth in claim 11, wherein the at least one of the constituents or amounts of materials in the traceable material composition does not modify the color or appearance of the glass container and are not visually detectable.

22. The method set forth in claim 16, wherein the traceable material composition does not modify the color or appearance of the glass container and is not visually detectable.

* * * * *